United States Patent [19]
Lengyel et al.

[11] Patent Number: 5,526,113
[45] Date of Patent: Jun. 11, 1996

[54] METHOD AND APPARATUS FOR MEASUREMENT OF SPATIAL SIGNAL AND NOISE POWER OF IMAGING SYSTEMS

[75] Inventors: J. Michael Lengyel, Ramona, Calif.; Randy M. Maner, Albuquerque, N.M.; Larry A. Nelson, Bellevue, Wash.

[73] Assignee: Honeywell Inc., Minneapolis, Minn.

[21] Appl. No.: 263,319

[22] Filed: Jun. 21, 1994

[51] Int. Cl.$^6$ .................................................. G01N 21/00
[52] U.S. Cl. .................................. 356/124.5; 356/239
[58] Field of Search .................... 356/237, 71, 124.5, 356/239

[56] References Cited

U.S. PATENT DOCUMENTS

| | | | |
|---|---|---|---|
| 3,657,550 | 4/1972 | Brown et al. | 250/217 CR |
| 3,788,749 | 1/1974 | George | 356/71 |
| 4,360,269 | 11/1982 | Iwamoto et al. | 356/239 |
| 5,072,314 | 12/1991 | Chang | 359/559 |
| 5,098,181 | 3/1992 | Akiyama | 351/221 |
| 5,105,380 | 4/1992 | Owechko | 364/825 |
| 5,109,533 | 4/1992 | Mine et al. | 455/63 |
| 5,120,123 | 6/1992 | Akiyama | 351/221 |

OTHER PUBLICATIONS

"Spatial Filtering and Optical Information Processing," Ch. 7 of *Introduction to Fourier Optics* by J. W. Goodman, McGraw–Hill Publishing Co., pp. 141–149 (1988).
"Measures of Image Quality" by L. A. Nelson et al., SID–91 Digest, pp. 768–771 (1991).
*Digital Picture Processing* by A. Rosenfeld et al., Second Edition, vol. 1, Academic Press, San Diego, pp. 75–78 (1982).
*The Fourier Transform and Its Applications* by R. N. Bracewell, McGraw–Hill Book Co., New York (1965) (no copy provided; suggested by inventor as background reference).

*Primary Examiner*—Richard A. Rosenberger
*Attorney, Agent, or Firm*—Kenneth J. Johnson; Ronald E. Champion

[57] ABSTRACT

A photographic facsimile of a line image at a predetermined orientation is illuminated by a collimated monochromatic light source to produce a diffraction pattern. The Fourier distribution of the diffraction pattern is focussed by a converging lens to image on a spatial frequency plane of spatial signal and spatial noise components. The image in the spatial frequency plane is applied to a detector for selectively measuring the spatial power contribution of the signal and noise components, thereby to provide a measure of image quality relating to imaging system signal-to-noise ratio. A spatial filter (18) may be introduced into the optical path to block the spatial signal components, while allowing the noise components to impinge on the detector. The line image is then reoriented in the image plane, and successive measurements of spatial signal and noise contributions repeated. The ratio of signal-to-noise power is then computed for each orientation of the line image. By simulating selected imaging components and generating a resultant line image, the effect of such components on noise may be determined.

11 Claims, 4 Drawing Sheets

METHOD AND APPARATUS FOR MEASUREMENT OF SPATIAL SIGNAL AND NOISE POWER OF IMAGING SYSTEMS

BACKGROUND OF THE INVENTION

1. Field of the Invention

The present invention generally relates to optical measurements, and, more specifically, to a method of and apparatus for measuring spatial signal power and spatial noise power of imaging system components by generating and separating the spatial noise and signal components of an image.

2. Description of the Prior Art

An image is herein defined as a specific pattern of light intended for human viewing. Image spatial noise is herein defined as light which was not intended to be in the image, but has been added to the image by the optical or electronic processes utilized to generate a visual display. Thus, the image spatial noise is derived by subtracting the intended image from the delivered image.

Images are presented for human viewing by printers, Cathode Ray Tube (CRT) displays, LCD displays, or may be created by many different other methods. By way of example, charge coupled device (CCD) cameras change scenes into electronic format which "creates" a series of images for transmission to a storage or reproduction device. Another method is to synthesize images within a computer. All these image sources may be electronically combined and the images thereby produced altered by electronic compression, storage and distribution, special coloration, etc. The image which is viewed on the CRT is the summation of all that precedes it. The resolution and image spatial noise ("jaggies", spurious patterning, and luminance irregularities) are limited by each contributor to the electronic images as well as by the display itself—therein lies the problem.

For many imaging systems it is difficult for the display system designer to identify the specific component or subassembly in the display system, e.g., the display head, symbol generator, transmission system, and sensors, that impairs the intended image, and to what degree the intended image was degraded or improved by implementing a design change. Heretofore the subject of image quality was based upon subjective measures, as visually observed by the operator (c.f. L. A. Nelson, R. M. Maner, M. J. Lengyel, M. Seo, *Measures of Image Quality*, Society for Information Display International Symposium Digest of technical papers, pp 768–771, 1991).

Image quality has historically been a subjective entity measurable only through psychophysical experimentation and statistical analysis of many observers' opinions. The psychophysical measures are extremely complex because chromatic, temporal, and luminance errors all contribute to perception of image quality. As these contributions are not readily measured in practice, comparisons between overall image quality determinations has heretofore not been feasible.

As a measure of image noise, image compression algorithms frequently refer to the total squared error between compressed and uncompressed images, where the error is determined by the difference between the input image and the reconstructed image following decompression. The problem with this method is that it is a metric which does not lend itself to a general characterization. The answer depends on the complexity of the input image. Further, the spatial distribution of noise energy such as spurious patterning is not described quantitatively by the squared error measurement, so that the measure cannot be correlated to perceived image quality.

The particular distribution of errors in an image profoundly affects the subjective impact of those errors. An example of this sensitivity is the impairment caused by addition of color subcarriers (NTSC, SECAM, PAL). By carefully planning and controlling the subcarrier frequencies relative to the scanning frequencies, the patterned noise subjectively observed is minimized. The magnitude of subcarrier is not the sensitive issue here. For a particular magnitude of subcarrier, the patterns it produces can be changed to be less subjectively impairing by the relative choice of frequencies.

Noise caused by external sources (such as switching power supplies) also causes image impairment. For equal energy, the patterned noise energy sources are much more impairing than noise energy sources which do not create spurious patterns in an image.

An apparatus and method of use is needed to characterize the spatial noise properties and spatial signal properties of an imaging system in a general sense, similar to noise measurements associated with time varying signals, where a particular input signal is applied and the resulting output is recorded and analyzed. By way of example, an audio engineer may use sine waves of selected frequencies and amplitudes to stimulate his audio system and measure the signal-to-noise power ratio using a spectrum analyzer. Similarly, a video engineer needs an instrument to measure the signal-to-noise power ratio of his video system component, so that a meaningful analytical measurement will guide changes within the video system and establish the level of performance based upon an objective measure of the imaging capability of the system. Here, we refer not to electronic noise power but to the spatial noise in the resulting output image.

While components in imaging systems are judged by the quality of a delivered image, no method or apparatus exists which accurately measures the spatial noise properties associated with a high quality image. The present invention defines one such property as the spatial signal to spatial signal-plus-noise power ratio. The present invention creates spatial frequency power spectrum representations by optical means from specially selected image primitives. The spatial image to power spectral density conversion is accomplished via an optical, two-dimensional Fourier transform of the input image. Using this transformation, the signal power and noise power are separable through spatial filtering. Measurements of these power terms enable signal/signal-plus-noise power ratio calculations which serve as an objective measure of spatial noise.

It is known that an image may be spatially filtered by performing an optical Fourier transformation of the input image and applying a spatial filter or mask at the Fourier image plane selectively to remove spatial frequency components. See, for example, J. W. Goodman, *Introduction to Fourier Optics*, McGraw-Hill, 1968, pp. 141–149. In U.S. Pat. No. 5,072,314, T. Y. Chang teaches selective amplification of spatial frequency components to provide enhancement of the features of an optically encoded image. The Fourier transform of the input image is a light distribution pattern in which the light intensity varies in accordance with the amplitudes of the spatial frequency components in the input signal, analogous to the Fourier transform of a complex electrical waveform into a plurality of sine waves, but in two dimensions. However, Chang does not measure the power of the spatial frequency components but, rather, reconstructs the image after amplifying selected spectral components, thereby enhancing the image.

In E. F. Brown, et al, U.S. Pat. No. 3,657,550, there is disclosed an apparatus for measuring the spatial response of optical systems (e.g., a television system). A display is generated in a cathode ray tube by means for varying the periodicity of a predetermined spatial waveform image. The optical system under test is disposed between the cathode ray tube and a masked aperture, with a photo-detector disposed behind the mask so as to provide an output proportional to the light intensity as the spatial waveform is slowly scanned with respect to the aperture. Brown et al does not teach the use of an optical Fourier transform to resolve the spatial components of the image as in the present invention, and his stimulus is different than is used for this measurement.

For the foregoing reasons, a need remains in the art for an apparatus and method of objectively determining the signal-to-noise ratio of imaging systems that provides a direct, quantitative measurement of the spatial noise quality of a displayed image and that is essentially independent of subjective influences.

SUMMARY OF THE INVENTION

The present invention is directed to an apparatus and method that satisfies the need for obtaining objective measurements of signal and noise power of imaging systems. An apparatus having features of the present invention comprises generating a photographic facsimile of a line image at a predetermined orientation and illuminating the photographic line image with a planar coherent monochromatic wavefront of light to produce a diffraction pattern. The diffracted light pattern provides an optical signal suitable for conversion from the spatial domain to the frequency domain. This is accomplished by passing the diffracted light pattern through a lens. The result presented in the focal plane of the lens is a distribution in space of spatial signal and noise components. A spatial filter is introduced into the optical path at the focal plane of the lens to block the signal components and allow passage substantially only of the noise components of the illuminated image. This filter may provide weighting of particular spatial frequencies in order to represent a particular reconstruction of the image, as, for example, by an observer's viewing conditions (i.e., close or far away). A detector is placed in the optical path of the light energy near the focal plane to provide a measure of the power of the signal component and the noise components.

The invention further provides for computing the power ratio of the magnitudes of the signal components and the noise components, thereby providing a signal-to-noise ratio.

In a preferred embodiment, the invention provides a light source for generating a large area beam of monochromatic coherent light defining an optical axis and passing through and around the line image, thereby forming a specific diffraction pattern unique to the line image. The diffracted light is passed through a lens which provides a spatial image to spectral power density transformation. A spatial filter has an opaque area configured so as to block the signal components and is positioned at the focal plane of the transform lens. The Fourier image disperses signal and noise components in a light pattern where the amplitude of respective spatial frequency components varies in accordance with the geometry (quality) of the input image. The filtered spatial frequency power distribution is captured by a magnifying lens and applied to a camera or other detecting device for recording the signal power amplitudes of the spatial signal and noise components.

The advantages of the present invention will be apparent to those skilled in the art from the following description, taken with reference to the accompanying drawings.

DESCRIPTION OF THE PREFERRED EMBODIMENT

Figure 1:
FIG. 1 is a schematic illustration of the effect of spatial noise contribution to the output image when digitizing an input image.
Figure 1:
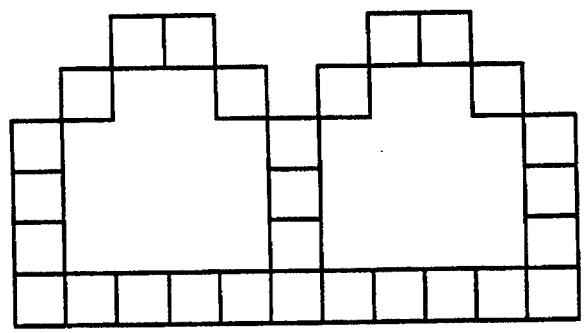
Figure 1:
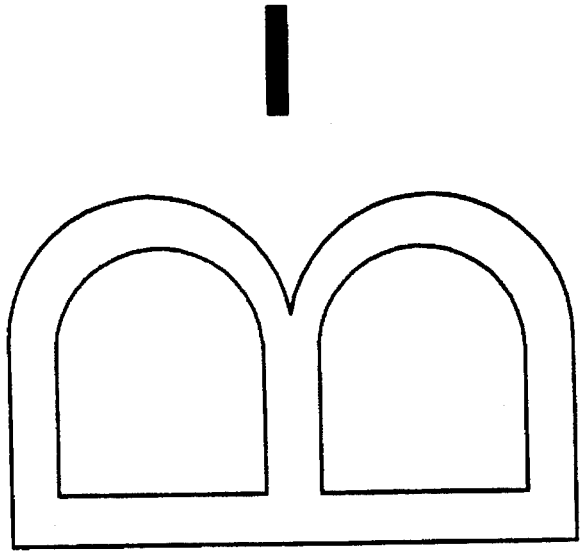

Modern imaging systems are sampled data systems. In order to process an image for storage in a memory array, or for transmission to a receiver, it must be digitized. A continuous picture may be represented by a finite string or array of numbers, denoted "samples". Sampling imposes restrictions on the system input according to the sampling structure, sampling density, and reconstruction method. The sampling used in imaging systems is usually multi-dimensional. Samples are stored which represent color, luminance, and motion (e.g., time sampling) for a two-dimensional (or possibly 3D) color image. Sampled display imagery consists of spatial signal and spatial noise. The best image is achieved when only spatial signal is perceived. In practical display applications, a tradeoff is made between resolving capability and acceptable spatial noise. Spatial noise is a consequence of the quantization or parceling of the physical space of the display. As shown in FIG. 1, it may be viewed as the light energy added to or subtracted from the intended image due to spatial quantization limitations. The power which corresponds to this spatial noise is separated from the spatial signal power by the present invention.

To facilitate an understanding of the invention, it is helpful to examine how an image is digitally formed and displayed, although a corresponding analysis may be made with respect to CRT displays. Referring now to FIG. 1, an image of the letter "B" is shown, and is seen to be formed of continuous straight and curved lines. The image typically will be stored in a frame buffer as a pattern of binary digital numbers which represent an array of picture elements or pixels, or displayed on a matrix display comprised of a plurality of rectangular picture elements which may be energized in accordance with the input image. The output image is then rendered as a plurality of discrete elements, here shown substantially rectangular in form. It will be clear to one skilled in the art that circular elements, such as result from a shadow mask CRT display, will produce an output image comprised of a plurality of substantially circular elements, and that the invention is not limited to particular geometric configurations. The resultant distortion of the input image may be characterized as spatial quantization error or spatial noise, and is shown in FIG. 1 as contributing spatial elements which add to or subtract from the input image. The noise components represent the difference between the quantized image and the original input image.

The fundamental principle for image processing as practiced in the present invention is that the power spectrum measures needed for an imaging system may be represented and captured as power intensity in space, rather than energy per unit time, since the delivered image or signal is distributed spatially. One cause of spatial noise is the inability of the display system to continuously position light energy, or the information which represents light energy, on a display surface (i.e., attributable to the finite addressability of the system).

Another type of spatial noise is caused by amplitude quantization (i.e., finite word length to describe the luminance level) which is idealized, but rarely measured, where real images are quantized.

The present invention enables a computation of spatial signal power to spatial signal plus noise power; the ratio of these power terms has been shown to be directly related to overall image quality for spatially quantized display surfaces. This normalized power ratio is bounded by 1, a perfect image, and 0, an imperceptible image.

The effective signal-to-noise ratio of an imaging system component can be measured by means of the two-dimensional Fourier transform capability of the present invention when the appropriate input images are used. Preferably the images (line images drawn at different angles on the display) used as inputs to the measuring system are captured photographically on positive black and white film. The line image is produced by the imaging system component being measured. A photographic facsimile of the line image is then used for the measurement. The line image effectively stimulates the imaging system device with an impulse orthogonal to the direction of the line, providing the maximum distribution of energy for that particular line orientation in the two-dimensional spatial frequency domain. This is analogous to the use of a unit impulse to excite a filter network in electronics. Clearly, an adequate characterization of the full range of potential power spectra presented on the face of the display cannot be achieved by measuring a single line in a single orientation. Thus, it is desirable to repeat the measurement of the line image on the display surface for every orientation, 0 through 180 degrees. In practice, it may be expedient to utilize larger rotational intervals, say 30° or less. Tabulating the results of the two-dimensional spatial frequency power spectra will provide information from which the signal-to-noise ratio of the imaging system device may be determined, in a manner to be described.

The mathematics which describe the spatial frequency representation of a sampled line image are complex. (See, e.g., A. Rosenfeld and A. Kak, *Digital Picture Processing*, Academic Press, Vol. 1, 2d ed., pp. 72–106). Although it is not necessary fully to understand such mathematics, it is helpful to understand two properties which are most easily explained thereby:

1. The Fourier transform of a sampling lattice or structure is another sampling lattice whose spacing and organization is dictated by the size and organization of the spatial domain sampling lattice.

2. The signal when applied to (i.e., drawn on) a sampling lattice in the spatial domain can be modeled mathematically as a multiplication of the signal function by the sampling lattice function. Consequently, in the spatial frequency domain this is a convolution of the Fourier transform of the signal with the transform of the sampling lattice. This convolution results in a replication of the Fourier transform of the signal at every position of the sampling lattice in the spatial frequency domain.

Figure 2:
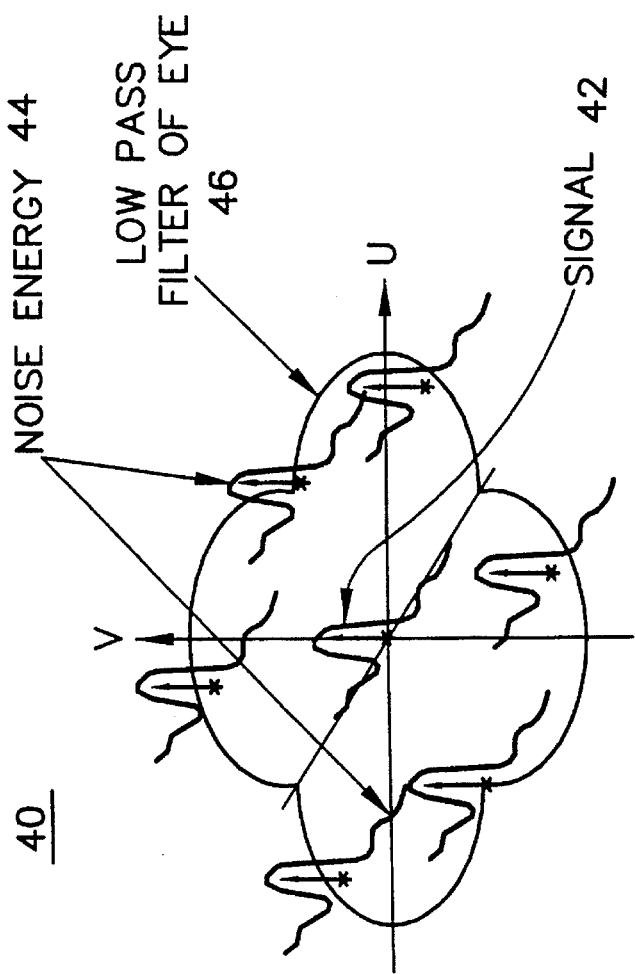
FIG. 2 is an illustration of the Fourier transformation of a line image into a frequency power spectrum distribution of signal and noise components.
Figure 2:
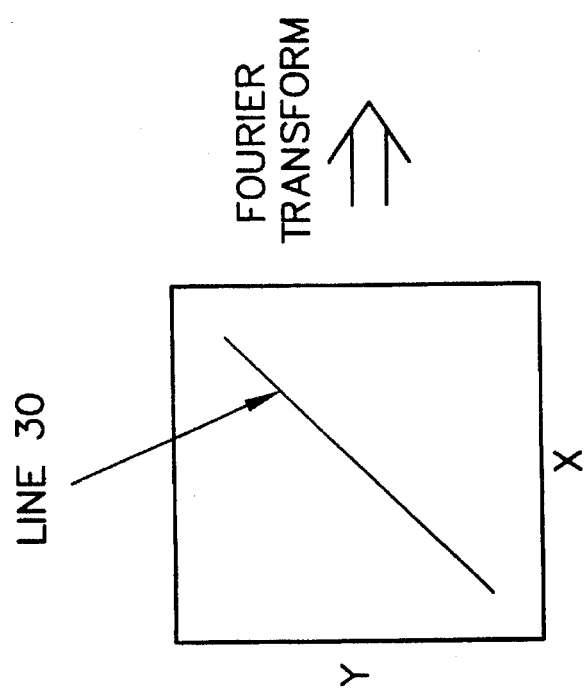

Given an infinite spatial sampling density of the displayed image (i.e., one that does not produce an interrupted or non-continuous image), only signal power is present in the two-dimensional spatial frequency components of this ideal line image. With finite sampling structures such as a shadow mask CRT or matrix displays, the power contained in the spatial frequency components of an actual two-dimensional sampled line image, as physically realizable, is a composite of the signal power plus the noise power, as illustrated in FIG. 2. The drawing shows a line image 30 disposed at a predetermined angular orientation, say 45 degrees, in the x-y plane. After an optical Fourier transformation, the line image is transformed into a centrally disposed signal component 42 and noise components 44, shown in the u-v plane of the spatial frequency domain. Contour 46 represents the limitation of the observed signal and noise amplitudes by the human eye, which acts as a low pass filter in the spatial frequency domain. Thus it is evident that the energy distribution which is not associated with the signal power (central replica) of the sampled image spectrum is the noise power. Separation of the signal power from the signal-plus-noise power (the total power) is done by spatial filtering. The central replica of the energy distribution pattern is physically blocked from view of the detector. A measurement of the remaining power yields the noise power. The signal power is calculated by subtracting the noise power from the total power, as the powers add algebraically.

Figure 3:
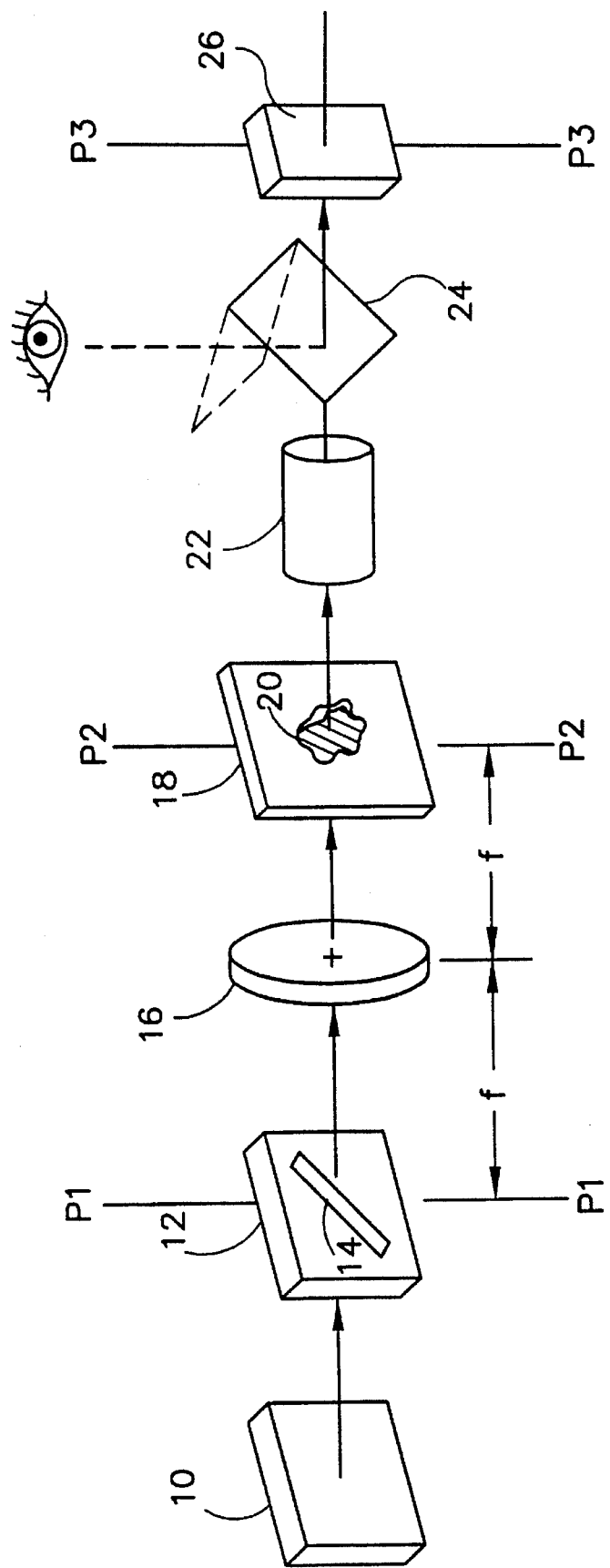
FIG. 3 is functional block diagram illustrating the optical components comprising the present invention.

Referring now to FIG. 3, there is shown in schematic form a functional diagram illustrating the optical components comprising the present invention. All of the optical components are mounted on an optical table which is supported by pneumatic isolation mounts (not shown). The components are aligned along the optical center line of the system as established by an axis defined by the center line of a beam expanding lens on a Helium Neon (HeNe) laser light source 10. The light source 10 is an expanded collimated laser operative at a wavelength which provides substantially planar coherent monochromatic irradiation. The intensity profile of the expanded collimated beam is approximately Gaussian.

A monochrome, positive film photograph of a line image 14 taken with a high quality medium format camera is used to generate the input to the optical analysis system. The positive film photograph is immersed in a liquid gate 12 which is a reservoir filled with a high quality optical oil that has an index of refraction which closely matches the index of the film. The liquid gate is well known (c.f. J. F. Goodman, supra, pp. 154–155) and is constructed of a housing containing a pair of optical flats which constrains the oil for receiving the film.

The planar light wave emanating from laser light source 10 is directed to the image plane P1 defined by the liquid gate 12 and photograph 14. There it is obstructed by the spatial line image and produces a far field or Fraunhofer diffracted pattern of the input image. The diffracted image pattern is focussed by a converging thin lens 16 where the Fourier transform of the input image is brought to a focus at the spatial frequency plane P2. The so-called "thin lens" is not necessarily thin in physical size, but rather denotes a lens which offers negligible transverse offset of an incident light ray. For this purpose, a collinear transmissive dual achromatic lens is suitable.

Figure 5:
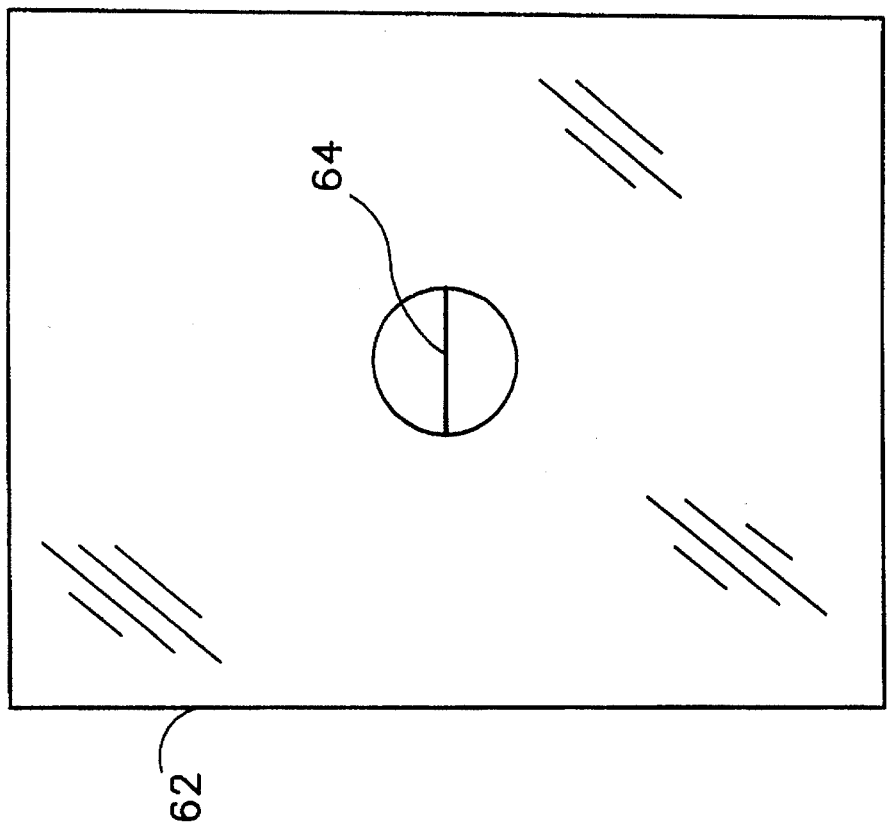
FIG. 5 shows a spatial filter in plan view used to measure noise power below the predetermined spatial frequency of FIG. 4.
Figure 4:
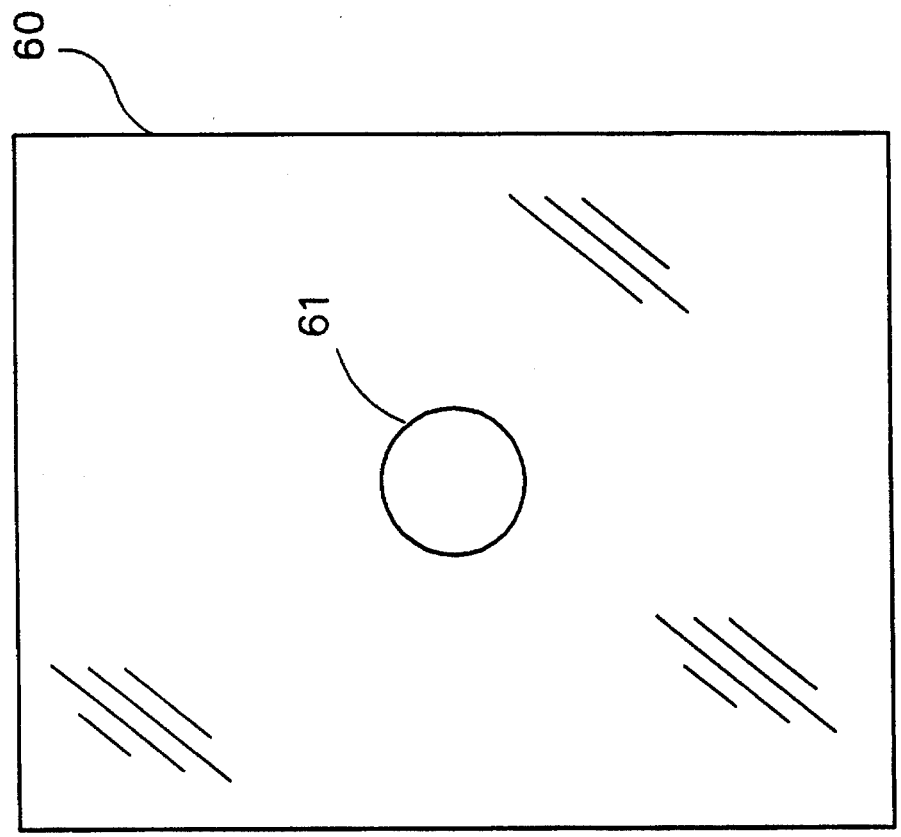
FIG. 4 shows a spatial filter in plan view used to measure total power below a predetermined spatial frequency.

Image noise power and image signal power are segregated at the spatial frequency plane P2 via the Fourier transform operation on the spatial image. The noise power may be separated for measurement from the signal power by a first spatial filter 60, as shown in FIG. 4. Spatial filter 60, which may be comprised of a metal plate of suitable thickness, is provided with a predetermined centrally disposed transmissive area 61 for selectively blocking spatial frequency components of the signal power. The diameter of the transmissive portion of the spatial filter defines a spatial frequency bandwidth for measuring total power (signal plus noise). The noise power may be separated for measurement from the signal power by a second spatial filter 62, provided with a centrally disposed opaque area 64, as shown in FIG. 5. The size and shape of the spatial filter is determined by the reconstruction function of the imaging system component, which is generally a low pass filter. The signal power term (i.e., the central replica) is physically blocked from view of the measuring device 26, which may be a medium format camera and a radiometer or a photodetector, when the noise power measurement is made. A high resolution CCD camera may also be used to store the output image for processing and analysis.

By knowing the physical size and geometry of the display or image source which created the input image, and by utilizing well-known Fourier transform theory, the Fourier transform of the input image can be determined. Using this information along with the physical size and geometry characteristics of the resultant Fourier spectra, the scaling factor needed to establish the size of the spatial filter can be determined.

For example, assume the input image was from a monochrome LCD which has a rectilinear organization of apertures which are spaced 0.001 inches apart in both the horizontal and vertical directions. The replicas in the Fourier plane would be separated by 1000 cycles per inch (1/0.001) according to Fourier theory. By measuring the physical distance between the centroids of neighboring replicas in the Fourier plane, a scale or ratio of physical distance to spatial frequency is established. Using this scale, the size of the spatial filter can be established at any arbitrary cutoff spatial frequency.

Magnification optics. 22, which may be a conventional macro lens, is used to aid in positioning the spatial filter and is left in place during measurement. Positioning of the spatial filter 18 is aided by use of the viewing optics 24 of the camera 26. As shown, the viewing optics comprise a folding mirror which deflects a portion of the incident light rays to the observer, and which is moved out of the optical path during the measurement.

Power measurements are made of the magnified spatial frequency power spectrum at the plane P3 of the camera film plane/detector sensor array. The sensing or recording area must be sufficiently large so as not to truncate or distort the transformed image required for the power measurements.

Two power quantities are measured: signal plus noise power (total power) and noise power. The noise power is algebraically subtracted from the total power to yield signal power. The ratio of signal power to noise power may then be computed for the image in question to derive the signal-to-noise ratio.

It will be clear to one skilled in the art that the invention allows one to compare different display systems on an equivalent basis, considering factors that influence the quality of the displayed image such as line writing algorithms, grey scale, sampling structure, sampling density, etc. It is also to be noted that the application of this invention is not limited to a display device, but that all components and subassemblies that influence the intended image will affect the measured values.

For imaging system components other than a display device, it is necessary to convert the output information of the component under test (which information is usually a set of digital data) into a real spatially distributed image. The information that represents the spatially distributed light energy may be converted into light energy and used as an input to the power measuring apparatus of FIG. 3 by devising a calibrated image simulator. Essentially, this is done by photographing the image simulator monitor displaying the converted image. Once accurately presented in visual form, a positive film photograph of the output visual information of the image simulator is used as the input image for the measurement system. The image simulator provides a spatial distribution of light energy that accurately represents the reconstructed output of the particular imaging system component under evaluation. Application of the present invention to this synthesized display system facilitates a signal-to-noise measurement of the discrete component in question. This will permit identifying the level of degradation associated with the component in the system, since it provides a quantitative measurement of its imaging capabilities.

This invention has been described herein in considerable detail in order to comply with the Patent Statutes and to provide those skilled in the art with the information needed to apply the novel principles and to construct and use such specialized components as are required. However, it is to be understood that the invention is not restricted to the particular embodiment that has been described and illustrated, but can be carried out by specifically different equipment and devices, and that various modifications, both as to the equipment details and operating procedures, can be accomplished without departing from the scope of the invention itself. Therefore, while the invention has been described in its preferred embodiments, it is to be understood that the words which have been used are words of description rather than limitation and that changes may be made within the purview of the appended claims without departing from the true scope and spirit of the invention in its broader aspects.

The embodiments of the invention in which an exclusive property or right is claimed are defined as follows:

1. A method of making image quality determinations by measuring spatial signal and noise power of an imaging system, comprising the steps of:

a) providing a monochromatic collimated beam of light;

b) providing a photographic facsimile of a displayed line image to be analyzed in a predetermined angular orientation;

c) illuminating said photographic facsimile by said light beam so as to provide a diffraction pattern thereof;

d) focussing a converging thin lens upon said diffraction pattern so as to produce a spatial frequency distribution thereof focussed on a spatial frequency plane, said spatial frequency distribution comprised of signal and noise spatial frequency components;

e) inserting a first spatial filter at said spatial frequency plane adapted for defining a predetermined spatial bandwidth and for transmitting said spatial signal and spatial noise frequency components;

f) focussing a magnifying lens upon said spatial plane whereby to produce a magnified image of said spatial frequency components;

g) applying said magnified image to a detector and measuring the spectral power of the detected spatial frequency components;

h) removing said first spatial filter and inserting a second spatial filter at said spatial frequency plane adapted for selectively blocking said signal spatial frequency component, and measuring the spectral power of the residual spatial frequency components;

I) applying a magnified image derived from said second spatial filter to said detector and measuring the spectral power of the residual detected spatial frequency components;

j) incrementally positioning said displayed line image to a further orientation and generating a corresponding photographic facsimile so as to provide a further diffracted image and selectively measuring the spectral power output of the corresponding spatial frequency components in the presence of said spatial filter;

k) repeating said incremental positioning of said line image to encompass a 360° rotation in the plane of said line image, and measuring the spectral power outputs corresponding thereto; and l) computing a ratio of the measured signal power to noise power at each of said incremental positions.

2. A method as set forth in claim 1, wherein said step of providing a line image to be analyzed comprises:

a) generating a signal corresponding to a line image to be displayed at a predetermined orientation;

b) processing said signal for storage in digital form;

c) transmitting said stored signal to a visual display; and d) photographing said visual display.

3. A method as set forth in claim 2, further comprising:

algebraically subtracting the value of said power of said second optical signal from the value of said power of said first optical signal to derive a third value representative of the power of said spatial signal; and deriving an algebraic ratio of said third value to said second value; whereat an optical signal-to-noise ratio is obtained.

4. Apparatus for measurement of spatial signal and noise power of an imaging system, comprising:

means for displaying a line image at a predetermined angular orientation;

means for providing a photographic facsimile of said line image;

light source means for providing a light beam along an optical axis for illuminating said photographic facsimile;

liquid optical gate means positioned along said optical axis for receiving said light beam and forming a diffracted representation of said line image;

a first optical element positioned along said optical axis for receiving said diffracted image and for focussing said diffracted image on a spatial frequency plane, whereat signal and noise components thereof are dispersed in a spatial light pattern wherein the amplitude and distribution of the spatial frequency components varies in accordance with the geometry of the diffracted image;

first spatial filter means introduced into said optical system means and positioned for producing a first optical signal comprised of said spatial signal component and said spatial noise component within a predetermined spatial bandwidth;

a second optical element focussed upon said spatial frequency plane for receiving said spatial light pattern, and for reproducing an image input upon said spatial frequency plane as an output image having magnified features corresponding to a plurality of spatial frequency components;

second spatial filter means for blocking said spatial signal component and thereby producing a second optical signal which is a spatial frequency distribution corresponding to said noise component of said illuminated image, said second spatial filter means being introduced at said spatial frequency plane and having a predetermined centrally disposed opaque area of predetermined transmissivity for selectively blocking spatial frequencies of said signal component; and means positioned to receive outputs of said first and second optical signals for detecting the relative powers thereof, where said means for detecting being responsive to said magnified features for providing a measure of the signal power incident thereupon.

5. Apparatus as set forth in claim 4, wherein said light source means comprises means for providing said light beam in the form of coherent light of a given wavelength and defining an optical axis.

6. Apparatus as set forth in claim 5, wherein said light source means comprises a helium neon (HeNe) laser for providing substantially monochromatic illumination.

7. Apparatus as set forth in claim 6, said first optical element comprising a converging thin lens.

8. Apparatus as set forth in claim 7, said liquid optical gate means comprising a pair of parallel optical flats defining a chamber for receiving a refractive-index matching oil superposed over said photographic facsimile and constrained between said optical flats.

9. Apparatus as set forth in claim 8, said second optical element comprising a macro lens and said means for detecting comprising a camera.

10. Apparatus as set forth in claim 8, said second optical element comprising a macro lens and said means for detecting comprising a radiometer.

11. Apparatus as set forth in claim 8, said second optical element comprising a macro lens and said means for detecting comprising a charge-coupled device array.

* * * * *